United States Patent
Sun et al.

(10) Patent No.: US 7,232,800 B2
(45) Date of Patent: Jun. 19, 2007

(54) DERIVATIVES OF MAGAININ AND METHODS OF PRODUCTION THEREOF

(75) Inventors: Yukun Sun, Shanghai (CN); Dengxi Wu, Shanghai (CN); Zhiyong Zhu, Shanghai (CN)

(73) Assignee: Shanghai Huayi Biotech Lab, Shanghai (CN)

( * ) Notice: Subject to any disclaimer, the term of this patent is extended or adjusted under 35 U.S.C. 154(b) by 501 days.

(21) Appl. No.: 10/705,106

(22) Filed: Nov. 10, 2003

(65) Prior Publication Data

US 2004/0197864 A1    Oct. 7, 2004

Related U.S. Application Data

(63) Continuation-in-part of application No. PCT/CN02/00317, filed on May 8, 2002.

(30) Foreign Application Priority Data

May 10, 2001 (CN) ............................... 01 1 12855

(51) Int. Cl.
*A61K 38/17* (2006.01)
*C12P 21/02* (2006.01)
*C07K 14/46* (2006.01)
*C07K 14/435* (2006.01)

(52) U.S. Cl. ................. 514/12; 435/71.3; 530/324

(58) Field of Classification Search .............. 514/12; 435/71.3; 530/324
See application file for complete search history.

(56) References Cited

U.S. PATENT DOCUMENTS 5,686,563 A * 11/1997 Kari ................. 530/326
5,792,831 A    8/1998  Maloy
5,912,231 A    6/1999  Houghten et al.
6,461,834 B1 * 10/2002 Dormady et al. ......... 435/68.1

OTHER PUBLICATIONS

Hwang et al. article entitled: "A Simple Method for the Purification of an Antimicrobial Peptide in Recombinant *Escherichia coli*" *Molecular Biotechnology*, vol. 18, 2001, pp. 193-198.
Lamb et al. article entitled: "Pexiganan Acetate" *Drugs*, Dec. 1998, 56 (6), pp. 1047-1052.

* cited by examiner

Primary Examiner—Jon Weber
Assistant Examiner—Rosanne Kosson
(74) *Attorney, Agent, or Firm*—Bell, Boyd & Lloyd LLP

(57) ABSTRACT

The present invention provides a Magainin derivative peptide and method of production thereof. Also provided is a pharmaceutically composition comprising said Magainin derivative peptide and pharmaceutically acceptable carrier and/or pharmaceutically compatible binding agents. The Magainin derivative peptide of the present invention having amino acid sequence of the general formula shown as below:

Gly-Ile-Gly-Lys-Phe-Leu-His-Ser-Ala-Lys-Lys-
Phe-Gly-Lys-Ala-Phe-Val-Gly-Glu-Ile-X-Asn-Y-Z-OH in which: X is an amino acid residue selected from the group consisting of Met, Ile and Leu; Y is an amino acid residue selected from the group consisting of Ser, Lys, Ile, Arg and Leu; and Z is Arg.

10 Claims, 2 Drawing Sheets

SEQUENCE LISTING

<160> NUMBER OF SEQ ID NOS: 15

<210> SEQ ID NO 1
<211> LENGTH: 24
<212> TYPE: PRT
<213> ORGANISM: Artificial sequence
<220> FEATURE:
<223> OTHER INFORMATION: Synthetic peptides

<400> SEQUENCE: 1

Gly Ile Gly Lys Phe Leu His Ser Ala Lys Lys Phe Gly Lys Ala Phe
1               5                   10                  15

Val Gly Glu Ile Met Asn Ser Arg
            20

<210> SEQ ID NO 2
<211> LENGTH: 24
<212> TYPE: PRT
<213> ORGANISM: Artificial sequence
<220> FEATURE:
<223> OTHER INFORMATION: Synthetic peptides

<400> SEQUENCE: 2

Gly Ile Gly Lys Phe Leu His Ser Ala Lys Lys Phe Gly Lys Ala Phe

```
                1               5                  10                  15
Val Gly Glu Ile Met Asn Lys Arg
            20

<210> SEQ ID NO 3
<211> LENGTH: 24
<212> TYPE: PRT
<213> ORGANISM: Artificial sequence
<220> FEATURE:
<223> OTHER INFORMATION: Synthetic peptides

<400> SEQUENCE: 3

Gly Ile Gly Lys Phe Leu His Ser Ala Lys Lys Phe Gly Lys Ala Phe
1               5                   10                  15

Val Gly Glu Ile Met Asn Arg Arg
            20

<210> SEQ ID NO 4
<211> LENGTH: 24
<212> TYPE: PRT
<213> ORGANISM: Artificial sequence
<220> FEATURE:
<223> OTHER INFORMATION: Synthetic peptides

<400> SEQUENCE: 4

Gly Ile Gly Lys Phe Leu His Ser Ala Lys Lys Phe Gly Lys Ala Phe
1               5                   10                  15

Val Gly Glu Ile Met Asn Ile Arg
            20

<210> SEQ ID NO 5
<211> LENGTH: 24
<212> TYPE: PRT
<213> ORGANISM: Artificial sequence
<220> FEATURE:
<223> OTHER INFORMATION: Synthetic peptides

<400> SEQUENCE: 5

Gly Ile Gly Lys Phe Leu His Ser Ala Lys Lys Phe Gly Lys Ala Phe
1               5                   10                  15

Val Gly Glu Ile Met Asn Leu Arg
            20

<210> SEQ ID NO 6
<211> LENGTH: 24
<212> TYPE: PRT
<213> ORGANISM: Artificial sequence
<220> FEATURE:
<223> OTHER INFORMATION: Synthetic peptides

<400> SEQUENCE: 6

Gly Ile Gly Lys Phe Leu His Ser Ala Lys Lys Phe Gly Lys Ala Phe
1               5                   10                  15

Val Gly Glu Ile Ile Asn Ser Arg
            20

<210> SEQ ID NO 7
<211> LENGTH: 24
<212> TYPE: PRT
<213> ORGANISM: Artificial sequence
<220> FEATURE:
<223> OTHER INFORMATION: Synthetic peptides

<400> SEQUENCE: 7
```

-continued

Gly Ile Gly Lys Phe Leu His Ser Ala Lys Lys Phe Gly Lys Ala Phe
1               5                   10                  15

Val Gly Glu Ile Ile Asn Lys Arg
            20

<210> SEQ ID NO 8
<211> LENGTH: 24
<212> TYPE: PRT
<213> ORGANISM: Artificial sequence
<220> FEATURE:
<223> OTHER INFORMATION: Synthetic peptides

<400> SEQUENCE: 8

Gly Ile Gly Lys Phe Leu His Ser Ala Lys Lys Phe Gly Lys Ala Phe
1               5                   10                  15

Val Gly Glu Ile Ile Asn Ile Arg
            20

<210> SEQ ID NO 9
<211> LENGTH: 24
<212> TYPE: PRT
<213> ORGANISM: Artificial sequence
<220> FEATURE:
<223> OTHER INFORMATION: Synthetic peptides

<400> SEQUENCE: 9

Gly Ile Gly Lys Phe Leu His Ser Ala Lys Lys Phe Gly Lys Ala Phe
1               5                   10                  15

Val Gly Glu Ile Ile Asn Arg Arg
            20

<210> SEQ ID NO 10
<211> LENGTH: 24
<212> TYPE: PRT
<213> ORGANISM: Artificial sequence
<220> FEATURE:
<223> OTHER INFORMATION: Synthetic peptides

<400> SEQUENCE: 10

Gly Ile Gly Lys Phe Leu His Ser Ala Lys Lys Phe Gly Lys Ala Phe
1               5                   10                  15

Val Gly Glu Ile Ile Asn Leu Arg
            20

<210> SEQ ID NO 11
<211> LENGTH: 24
<212> TYPE: PRT
<213> ORGANISM: Artificial sequence
<220> FEATURE:
<223> OTHER INFORMATION: Synthetic peptides

<400> SEQUENCE: 11

Gly Ile Gly Lys Phe Leu His Ser Ala Lys Lys Phe Gly Lys Ala Phe
1               5                   10                  15

Val Gly Glu Ile Leu Asn Ser Arg
            20

<210> SEQ ID NO 12
<211> LENGTH: 24
<212> TYPE: PRT
<213> ORGANISM: Artificial sequence
<220> FEATURE:
<223> OTHER INFORMATION: Synthetic peptides

<400> SEQUENCE: 12

```
Gly Ile Gly Lys Phe Leu His Ser Ala Lys Lys Phe Gly Lys Ala Phe
1               5                   10                  15

Val Gly Glu Ile Leu Asn Lys Arg
            20

<210> SEQ ID NO 13
<211> LENGTH: 24
<212> TYPE: PRT
<213> ORGANISM: Artificial sequence
<220> FEATURE:
<223> OTHER INFORMATION: Synthetic peptides

<400> SEQUENCE: 13

Gly Ile Gly Lys Phe Leu His Ser Ala Lys Lys Phe Gly Lys Ala Phe
1               5                   10                  15

Val Gly Glu Ile Leu Asn Ile Arg
            20

<210> SEQ ID NO 14
<211> LENGTH: 24
<212> TYPE: PRT
<213> ORGANISM: Artificial sequence
<220> FEATURE:
<223> OTHER INFORMATION: Synthetic peptides

<400> SEQUENCE: 14

Gly Ile Gly Lys Phe Leu His Ser Ala Lys Lys Phe Gly Lys Ala Phe
1               5                   10                  15

Val Gly Glu Ile Leu Asn Arg Arg
            20

<210> SEQ ID NO 15
<211> LENGTH: 24
<212> TYPE: PRT
<213> ORGANISM: Artificial sequence
<220> FEATURE:
<223> OTHER INFORMATION: Synthetic peptides

<400> SEQUENCE: 15

Gly Ile Gly Lys Phe Leu His Ser Ala Lys Lys Phe Gly Lys Ala Phe
1               5                   10                  15

Val Gly Glu Ile Leu Asn Leu Arg
            20
```

DERIVATIVES OF MAGAININ AND METHODS OF PRODUCTION THEREOF

CROSS-REFERENCE TO RELATED APPLICATION

This application is a continuation-in-part of PCT/CN02/00317, which bears an international filing date of May 8, 2002 and claims priority to Chinese Application No. 01112855.0 filed May 10, 2001.

BACKGROUND OF THE INVENTION

There are many life forms, for example, insects, microorganisms, amphibians and human beings which may produce anti-bacterial peptide materials that protect their communities. These anti-bacterial peptides can penetrate lipids on the cell membranes and make them inactive, can also affect protozoon species, germ cells and even viruses, hence such peptides are referred to as super-antibiotics. Anti-bacterial peptides all carry various amounts of positive charge, and their anti-bacterial mechanism lies in the combination of the positive charges carried by the peptides with the negative charges carried by the phospholipids which exist in the bacteria cell wall, creating an ion path on the cell membrane, enhancing the penetrability, causing the bacteria to dissolve and die. Hence the anti-microbial activities of these peptides do not depend on the binding with any specific receptors.

The anti-bacterial peptides exhibit a broad spectrum of antimicrobial activity upon gram-positive and gram-negative bacteria, as well as aerobic and anaerobic bacteria. They are different from antibiotics in that anti-bacterial peptides do not produce drug-resistance effects, even bacteria that have resistance to many types of antibiotics could be suppressed by the anti-bacterial peptides. Further, such anti-bacterial peptides also have inhibitive effect to protozoon species and viruses. As the metabolism products of the anti-bacterial peptides are amino acids, these peptides are of low toxicity for host cells. In summary, the anti-microbial peptides are a class of compounds with wide prospects of being used for anti-microbial drugs.

Magainins are a category of naturally occurring anti-bacterial peptides derived from frog skin with anti-bacterial effects. Magainins has been extensively studied up till now, they have such features as being easy to be synthesized, low in cost and little possibility of hemolysis.

U.S. Pat. No. 5,589,364 disclosed a method by which the Magainin II peptide having 23 amino acids can be prepared using bioengineering, techniques. Magainin II (hereinafter referred as naturally occurring Magainin, wild-type Magainin or Magainin) is a type of the naturally occurring frog-skin anti-bacterial peptide, having amino acid sequence shown as below:

[SEQ ID NO.:17]
Gly-Ile-Gly-Lys-Phe-Leu-His-Ser-Ala-Lys-Lys-
Phe-Gly-Lys-Ala-Phe-Val-Gly-Glu-Ile-Met-Asn-Ser-OH in which:

Gly stands for glycine, Ile for isoleucine, Lys for lysine, Phe for phenylalanine, Leu for leucine, His for histidine, Ser for serine, Ala for alanine, Val for valine, Glu for glutamic acid, Met for methionine and Asn for asparaginate.

U.S. Pat. No. 6,183,992 disclosed a method to produce MSI-78 (22 amino acids), a derivative of magainin, having the amino acid sequence shown as below:

[SEQ ID NO.:18]
Gly-Ile-Gly-Lys-Phe-Leu-Lys-Lys-Ala-Lys-Lys-Phe-
Gly-Lys-Ala-Phe-Val-Lys-Ile-Leu-Lys-Lys-NH$_2$

It has been reported in ADIS NEW DRUG PROFILE by Harriet M. Lamb, etc., that the Magainin derivative MS1-78 shows obvious curative effect in treating trauma infection and crura ulceration caused by the diabetes mellitus.

BRIEF DESCRIPTION OF THE INVENTION

One aspect of the present invention provides Magainin derivative peptides having the property of anti-microbial effect.

In one embodiment, the invention is directed to Magainin derivative peptides in which Arg is added to the C-terminus of the naturally occurring Magainin for a cleavage reagent while preserving the anti-microbial activity of the Magainin peptide. In this embodiment, the cleavage reagent includes alkaline protease such as trypsin and clotrispain.

In another embodiment, the present invention is directed to fusion peptides comprising at least two tandemly linked Magainin derivative peptides that are altered preferably by adding Arg at the C-terminus of the peptides while preserving the anti-microbial activity, as well as isolated DNA sequences comprising a DNA sequence encoding these peptides, expression vectors comprising these isolated DNA sequences, and transformed host cells comprising these expression vectors.

Another aspect of the present invention provides the recombinant and synthetic methods of producing these Magainin derivatives.

In one embodiment, the present invention includes a method for producing the Magainin derivative peptide of claim 1, either by expressing a single copy of the Magainin derivative in an expression vector or, alternatively, by expressing a fusion protein containing multiple copies of the Magainin derivative and then cleaving this fusion protein into individual copies of the Magainin sequence using the appropriate cleavage reagent. Cleavage reagents include, but are not limited to, alkaline proteases such as trypsin and clotrispain.

In another embodiment, the present invention includes a method for producing the Magainin derivative peptide of claim 1 by solid phase synthesis, which comprises of using HMP resin as a solid phase carrier, protecting alpha-amine of an amino acid with 9-fluorenyl methoxycarbonyl (Fmoc), synthesizing on a peptide synthesizer, and obtaining the peptide after the steps of separation, purification and lyophilization.

In another aspect, the present invention provides a pharmaceutical composition comprising the Magainin derivative peptide of claim 1 and pharmaceutically acceptable carrier and/or pharmaceutically compatible binding agents.

In yet another aspect, the present invention provides a method for the treatment of a patient having need of the Magainin derivative peptide of claim 1 comprising: administrating to said patient a therapeuticaly effective amount of the peptide of claim 1.

DETAILED DESCRIPTION OF THE INVENTION

Figure 1:
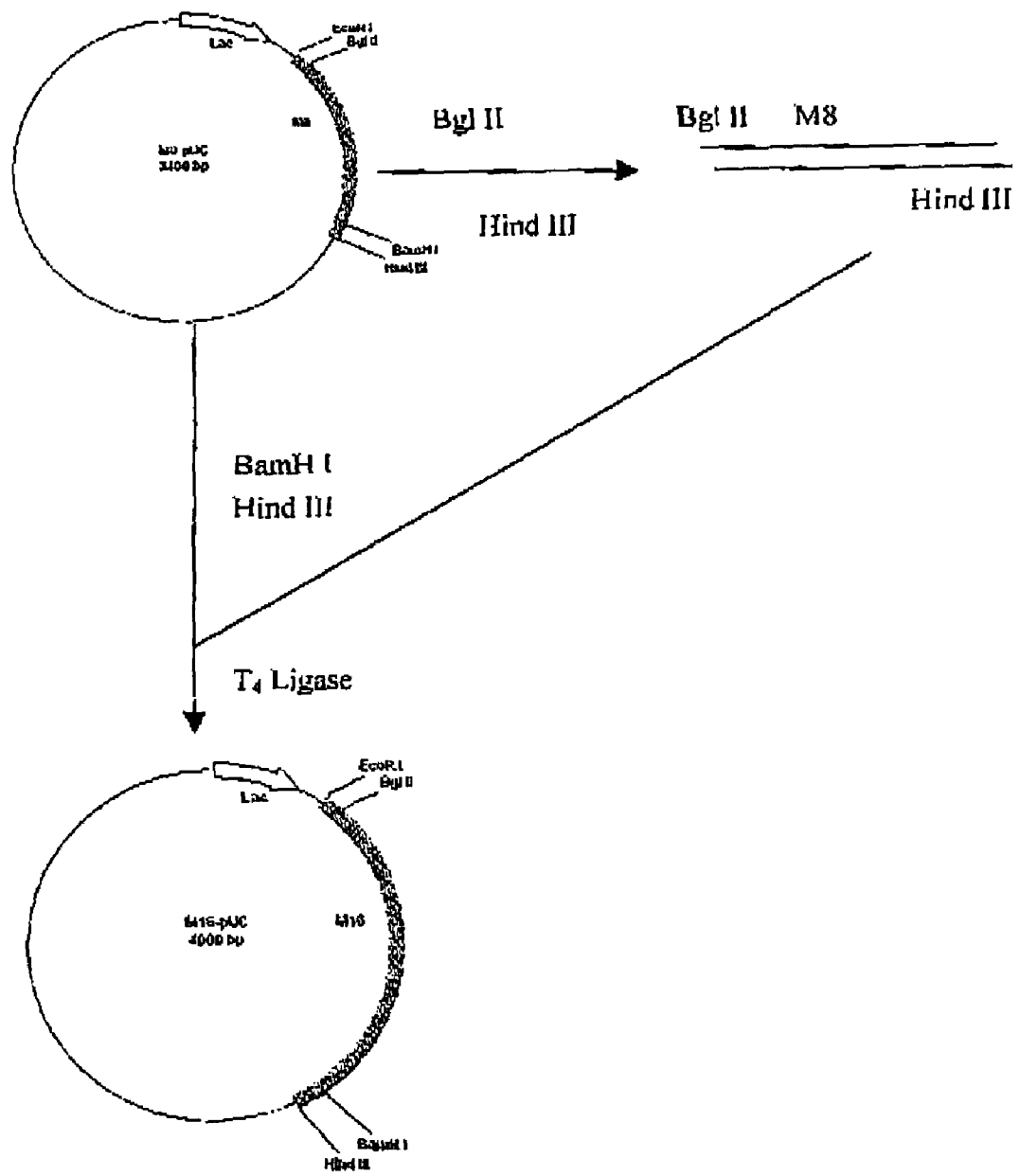
FIG. 1 depicts the process used to construct a plasmid containing 1 to 16 copies of the gene encoding the Magainin derivative peptide.
Figure 2:
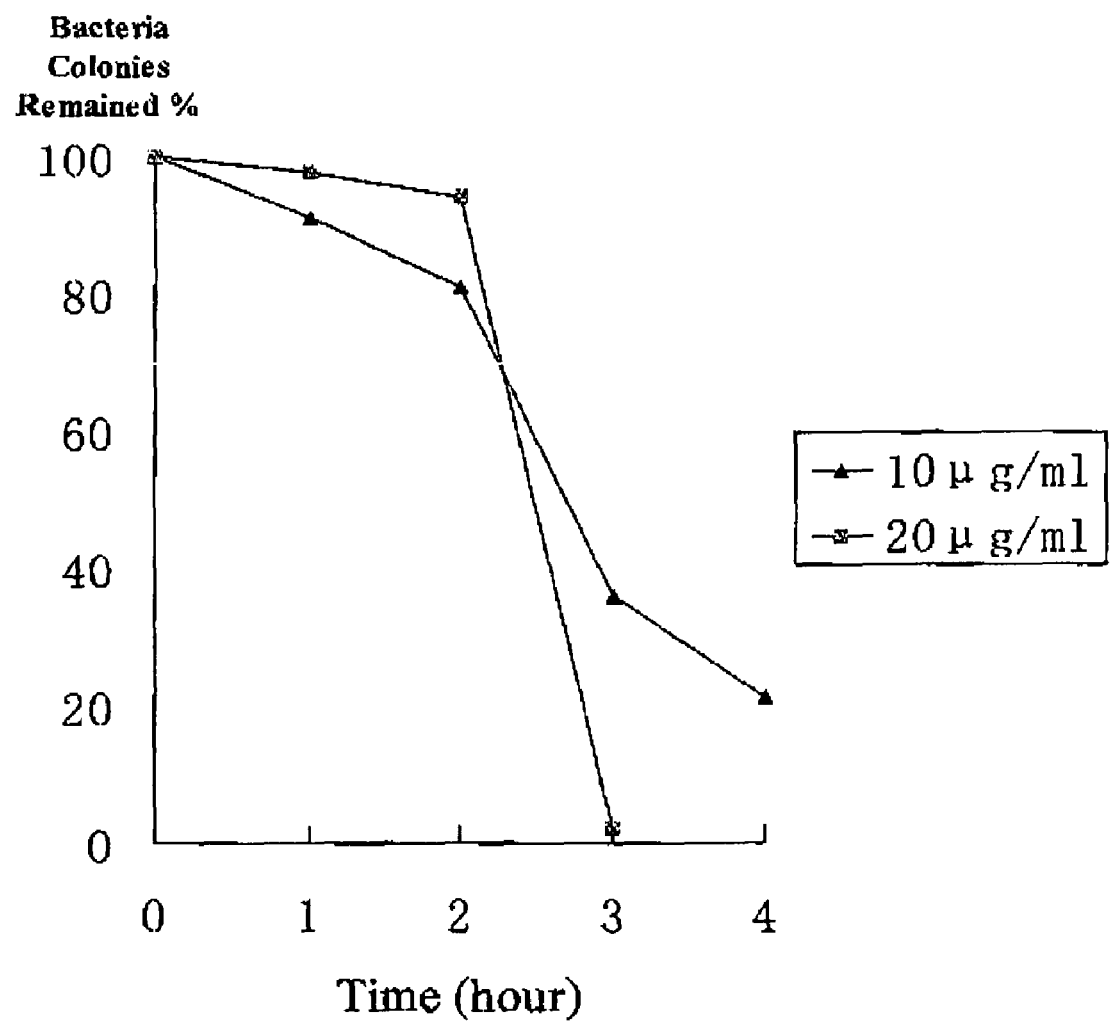
FIG. 2 shows the result of the time-kill study of Magainin (Leu$_{21}$, Ser$_{23}$, Arg$_{24}$) on *Escherichia coli*.

The present invention is directed to novel Magainin derivatives with anti-microbial properties, and to recombinant and synthetic methods for producing these Magainin derivatives. The recombinant methods encompass both methods directed to single copies of the genes for these peptides, and, preferably, to multiple copies of these genes that are tandemly linked so as to produce fusion proteins which are then cleaved to produce multiple copies of the desired peptide.

In the latter case, one embodiment of the present invention is specifically directed to the alteration of the sequences of these peptides to allow for the cleavage of the multimeric fusion proteins produced by these methods by trypsin, which normally is specific for either Arg or Lys residues. In the methods of the invention, Arg is preferably added to the C-terminus of each gene, and any Lys residues internal to these genes are reversible protected to prevent such residues from trypsin cleavage.

The present invention is also directed to various pharmaceutical formulations containing the Magainin derivatives of the present invention. Formulations containing those active compounds have therapeutic utility, particularly in the treatment of disease caused by microbial infection.

In the present invention, "anti-microbial" peptides are peptides with Magainin-like anti-microbial activity, i.e., peptides that have inhibitory property to bacterial reproduction or proliferate. Assays for such activity are well known to the skilled artisan, and are described elsewhere herein (see, e.g., the anti-microbial assay models provided in the examples). Anti-microbial peptides contemplated herein include Magainin, and analogs and derivatives thereof, including the specific analogs and derivatives disclosed elsewhere herein. As intended herein, "derivatives," "analogs," and "variants" are used synonymously.

Sequences of Magainin Derivatives

The present invention is directed to derivatives of the naturally occurring Magainin, which has the amino acid sequence as below:

[SEQ ID NO.:17]
Gly-Ile-Gly-Lys-Phe-Leu-His-Ser-Ala-Lys-Lys-Phe-
Gly-Lys-Ala-Phe-Val-Gly-Glu-Ile-Met-Asn-Ser-OH

In one aspect of the invention, the derivatives of Magainin contemplated have amino acid sequences of the general formula as below:

[SEQ ID NO.:16]
Gly-Ile-Gly-Lys-Phe-Leu-His-Ser-Ala-Lys-Lys-Phe-
Gly-Lys-Ala-Phe-Val-Gly-Glu-Ile-Xaa-Asn-Xaa-Arg-OH

In which:
Xaa at position 21 is an amino acid selected from the group consisting of Met, Ile and Leu; Xaa at position 23 is an amino acid selected from the group consisting of Ser, Lys, Ile, Leu and Arg.

Of particular interest are the Magainin derivatives of SEQ ID NOs:1-15, which are shown elsewhere herein to exhibit particularly advantageous properties. As set forth in the present invention, the Magainin derivatives contemplated herein may be prepared by synthetic chemical means, and by less expensive recombinant techniques that are novel to the present invention.

In the present invention, Magainin derivatives are generally referred to either by SEQ ID NO, or, alternatively, by following the name "Magainin" with a designation within parentheses of each changed amino acid position in the sequence, where the new amino acid(s) at each changed position is/are given, followed by a subscript indicating the position of the change(s) relative to the N-terminal amino acid of the peptide. Thus, in this alternative nomenclature, SEQ ID NO:1 may also be designated as Magainin (Met$_{21}$, Ser$_{23}$, Arg$_{24}$).

Other Magainin derivatives contemplated herein include, e.g.: Magainin (Met$_{21}$, Lys$_{23}$, Arg$_{24}$) (SEQ ID NO: 2); Magainin (Met$_{21}$, Arg$_{23}$, Arg$_{24}$) (SEQ ID NO: 3); Magainin (Met$_{21}$, Ile$_{23}$, Arg$_{24}$) (SEQ ID NO: 4); Magainin (Met$_{21}$, Leu$_{23}$, Arg$_{24}$) (SEQ ID NO: 5); Magainin (Ile$_{21}$, Ser$_{23}$, Arg$_{24}$) (SEQ ID NO: 6); Magainin (Ile$_{21}$, Lys$_{23}$, Arg$_{24}$) (SEQ ID NO: 7); Magainin (Ile$_{21}$, Ile$_{23}$, Arg$_{24}$) (SEQ ID NO: 8); Magainin (Ile$_{21}$, Arg$_{23}$, Arg$_{24}$) (SEQ ID NO: 9); Magainin (Ile$_{21}$, Leu$_{23}$, Arg$_{24}$) (SEQ ID NO: 10); Magainin (Leu$_{21}$, Ser$_{23}$, Arg$_{24}$) (SEQ ID NO: 11); Magainin (Leu$_{21}$, Lys$_{23}$, Arg$_{24}$) (SEQ ID NO: 12); Magainin (Leu$_{21}$, Ile$_{23}$, Arg$_{24}$) (SEQ ID NO: 13); Magainin (Leu$_{21}$, Arg$_{23}$, Arg$_{24}$) (SEQ ID NO: 14) and Magainin (Leu$_{21}$, Leu$_{23}$, Arg$_{24}$) (SEQ ID NO: 15).

The Magainin derivatives of this invention are amphoteric (synonymous with amphiprotic) compounds, and may be sufficiently acidic or sufficiently basic to react with any of a number of inorganic bases, and inorganic and organic acids, to form a salt. Acids commonly employed to form acid-addition salts are inorganic acids such as hydrochloric acid, hydrobromic acid, hydrolodic acid, sulfuric acid, phosphoric acid, aid the like, and organic acids such as p-toluene-sulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebucate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, mnethanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and, especially, hydrochloric acid.

Alkalis may also be employed to react with derivatives of this invention to form salts. Representative examples of such alkalis include ammonium, alkali metals, alkali metal hydroxides, carbonates, and bicarbonates. Typically, such an alkali may be sodium hydroxide, potassium hydroxide, ammonium hydroxide, and potassium carbonate.

One aspect of the present invention provides a method to produce an Magainin derivative peptide thereof by solid phase synthesis, which comprises of using HMP resin as a solid phase carrier, protecting the alpha-amine of an amino acid with 9-fluorenyl methoxycarbonyl (Fmoc), synthesizing the peptide on a peptide synthesizer by the amino acid sequence of an Magainin derivative, and obtaining the peptide after separation, purification and lyophilization. For example, all the Magainin derivative peptides of the present invention may be synthesized by such chemical methods.

In another aspect, the present invention provides a method to produce a Magainin derivative peptide by recombinant techniques. In one embodiment, such techniques comprise: synthesizing gene fragments by the amino acid sequence of an Magainin derivative; ligating the synthesized gene fragments; constructing a recombinant plasmid, culturing suitable bacterial host cells and transforming the recombinant plasmid into the bacterial host cells; extracting the inclusion bodies after fermentation of the bacteria strain and collapse of cell walls; and, obtaining the final product after lysing the inclusion bodies, separating rough product followed by HPLC purification and lyophilization.

Although the present invention discusses the construction of the desired Magainin derivative gene of interest via synthetically produced DNA fragments, also contemplated herein are any suitable method for producing the gene of interest, e.g., by mutagenesis of the wild-type Magainin gene, or any other method known to the skilled artisan.

In an additional embodiment, the present invention contemplates a recombinant method comprising: constructing an expression vector comprising at least two tandemly linked Magainin derivative DNA sequences and a promoter sequence, wherein the promoter sequence is capable of driving the expression of the tandemly linked Magainin derivatives DNA sequences; expressing the expression vector in a host cell to produce a fusion protein comprising at least two tandemly linked Magainin derivative peptide sequences; and, cleaving the resulting fusion protein into separate Magainin derivative peptides.

In one aspect of the present invention, recombinant methods may be used to produce monomers of the Magainin peptide derivatives of interest, e.g., monomers of the Magainin peptide derivatives of the invention. In another aspect, the present invention is drawn to the production by recombinant methods of fusion proteins of the Magainin peptide derivatives of interest, e.g., multimeric fusion proteins of the Magainin peptide derivatives of the invention, In such tandemly linked Magainin or Magainin derivative constructs, "tandemly linked" or "tandem linkage" as it refers to the peptides of the invention is used to indicate any linkage between the peptides of interest that allows for the production of a single fusion protein that may be cleaved by the appropriate cleavage reagent to produce separate peptides of the desired sequence. As described below in the discussion of Magainin, such cleavage reagents include, e.g., alkaline proteases such as trypsin and clotrispain.

In the present invention "tandemly linked" or "tandem linkage" is also used to refer to the joining of DNA sequences of the invention. In this context, "tandemly linked" DNA sequences are DNA sequences that are so joined that they serve as the template for the production by transcription/translation of a tandemly linked fusion peptide.

In one embodiment of the present invention, two or more Magainin derivative sequences may be tandemly linked without a spacer sequence. As an example, two Magainin derivative sequences in which an Arg residue has been added to the C-terminus (e.g., any of SEQ ID NOs:1–15) may be tandemly linked such that the Arg at the C-terminus of the first Magainin derivative sequence is followed by the Gly at the N-terminus of the next Magainin derivative sequence. Similar tandem linkage of more copies of such Magainin derivative sequences allow for the production of a fusion protein in which N copies of the Magainin sequence are repeated. In these constructs, treatment with, e.g., trypsin, will cleave the fusion protein after each C-terminal Arg residue to produce separate Magainin derivative sequences.

In another embodiment, Magainin derivative sequences may be tandemly linked with an amino acid spacer of Xaa . . . Xaa between the C-terminus of one peptide and the N-terminus of the next peptide in the fusion protein. In this circumstance, in order for the fusion proteins containing tandemly linked Magainin derivative sequences to be correctly cleaved to produce separate peptides of the desired sequence, it is necessary that cleavage does not occur within these sequences, while the spacer amino acid Xaa . . . Xaa is cleaved from linking with the C-terminus or the N-terminus of any desired separate peptide.

With regard to using trypsin as a cleavage reagent, any of the internal $Lys_4$, $Lys_{10}$, $Lys_{11}$ and $Lys_{14}$ amino acid residues of the wild-type Magainin sequence that are present in the fusion protein should be protected from being cleaved. Thus in instances where the cleavage reagent has an internal recognition site or sites within the Magainin derivatives of the fusion protein, it will be necessary to protect the internal Lys within these sequences. For example, acetylation methods as described elsewhere herein may be used to protect internal Lys residues, thereby removing them after trypsin cleavage.

In making substitutions to the Magainin sequence, it is important to maintain the activity of the Magainin derivatives produced by such substitutions. Such conservation of activity may be made based on predictions as to appropriate substitute amino acid residues, for example based on conservative or highly conservative amino acid substitutions. Predictions of appropriate amino acid substitutions may also be made based on data regarding sequence conservation at particular amino acid positions.

Alternatively, substitutions that maintain the activity of the Magainin derivatives produced by such substitutions may be identified by the screening of Magainin derivatives for Magainin-like activity. Specifically, random or directed mutations in the Magainin sequence produced by standard means may be screened for their effect on the activity of the resulting Magainin derivative peptide by activity assays appropriate for Magainin. In this regard, "Magainin-like activity," as used herein, refers to anti-microbial activity exhibited by Magainin in any of the assays disclosed elsewhere herein.

As used herein, "derivatives," "analogs," and "variants" are used synonymously to refer to sequences derived from and related to the Magainin sequence, as described in detail below. Specific examples of Magainin derivatives contemplated herein include the sequences of SEQ ID NOs:1–15.

In accordance with a preferred embodiment of the present invention, Magainin derivative peptides also include any of the above-described sequences modified to have at least 85% percent similarity, preferably 90% similarity, while preserving Magainin-like activity. For example, derivatives may include sequences in which, in addition to an Arg added to the C-terminus, have up to three amino acid changes while still retaining Magainin-like activity. Such small changes in sequence would be well-known to one of ordinary skill in the art. Examples of such changes may be found in the relevant literature for Magainin peptides.

Also contemplated as included within the term "Magainin derivatives" are Magainin derivative sequences that are further modified by any of the modifications known to the skilled artisan, particularly those modifications that improve the properties of the Magainin derivative, e.g., the half-life of the peptide.

As contemplated herein, "Magainin derivatives" also encompasses wild-type Magainin sequences where modifications are made not to the amino acid sequence itself, but to the side-chains of the amino acids, i.e., by cross-linking of reagents known to one of ordinary skill in the art, etc.

Recombinant Method for Producing Magainin Derivatives

The recombinant techniques used to prepare constructs, expression vectors, transformed cells, and purified fusion proteins of such Magainin derivatives are described as below. Specific examples of the use of recombinant techniques to prepare monomeric or multimeric peptides of the Magainin derivatives of the invention are provided in the Examples.

It is well known that one amino acid may be encoded by multiple codons. Thus a Magainin derivative DNA sequence, as used herein, refers to any DNA sequence that encodes a specified Magainin derivative peptide sequence. One skilled in the art can deduce and synthesize various DNA sequences and sequence combinations encoding Magainin derivative. In the present invention, codons with high frequency in E. Coli are preferred.

Vectors suitable for carrying the DNA sequences encoding Magainin derivative can be chromosome-derived, non-chromosome-derived, or synthetic DNA. These vectors may include, but are not limited to, microphage DNA, bacillus virus, bacterial plasmid, yeast plasmid, and vectors derived from a combination of phage, plasmid and viral DNA. The viral DNA may include, but is not limited to, bovine and poultry small pox virus, adenovirus, and pseudorabies virus. Many other suitable vectors are well known to one skilled in the art. Any plasmid or vector that exist and replicates stably in host cells may he used in this invention.

Representative but non-limiting examples of the expression vectors contemplated in the present invention include those used in bacterial systems, such as commercially available plasmids pKK233-2, pKK223-3, pEZZ18, pUC18, pUC19, and pT7 (Amersham Pharmacia Biotech).

In the present invention the target gene is linked to an appropriate promoter on an expression vector. A promoter is a sequence that can regulate and control gene transcription i.e., is capable of driving the expression of a protein sequence using a DNA template. The representative examples of promoter include lac, trp, tac of E. Coli; T7 of phage; $P_L$ of λ phage, and other known promoters existing in prokaryotic cells, eukaryotic cells, and viruses that control gene expression. Particularly preferred bacterial promoters include lacI, lacZ, T3, T7, Protein A signal peptide, gpt, $\lambda P_R$, $P_L$ and trp. The selection of appropriate promoters is apparent to one skilled in the art.

In addition, the preferred expression vector may have one or more selection marker gene(s) in order to facilitate screening of the host cells. Such marker genes include tetracycline and penicillin resistance genes in E. Coli, and dihydrofolate reductase and neomycin resistance genes in eukaryotic expression systems.

The expression vectors of the present invention may contain N copies of the genes linked in tandem, in which N is an integer from 1 to 16. Preferably, N is an integer from 2 to 8. More preferably, N is either 4 or 8. Thus in one preferred embodiment of this invention, the expression vector contains 1 copy of Magainin derivative. In another preferred embodiment of this invention, the expression vector contains 2 copies of Magainin derivative linked in tandem. In another preferred embodiment of example presented in this invention, the expression vector contains 4 copies of Magainin derivative linked in tandem. In another preferred embodiment of this invention, the expression vector contains 8 copies of Magainin derivative linked in tandem. In another preferred embodiment of this invention, the expression vector contains 16 copies of Magainin derivative linked in tandem.

The vectors of the present invention carrying multiple copies of gene(s) and appropriate promoters or other gene expression regulatory components can be transformed into appropriate host cells to express the fusion proteins in the host cells. Therefore, this invention also relates to host cells that are capable of expressing Magainin derivative polypeptides. The expression vector can be introduced into host cells by genetic engineering method such as transformation, transfection, or infection. For example, the expression vector may be introduced via transformation with calcium chloride, transfection in the presence of DHAE-dextran as a carrier, or by electroperforation. These methods will efficiently transfer the vector containing multiple copies of gene(s) of the present invention into host cells. The vectors referred to herein can be plasmids, viral particles, or bacterial phages.

Suitable host cells may include, but are not limited to, bacterial cells such as E. Coli, streptococcus, salmonella, and eukaryotic cells such as yeast. The selection of the appropriate host cells is apparent to one skilled in the art. For the purpose of lowering production cost, prokaryotic cells are the preferred host cells. Representative examples include a variety of strains of E. coli, e.g., JM103, JM109, HB101, and DH5α.

The host cells of the present invention contain an expression vector containing N copies of a gene encoding Magainin derivative peptides, in which N is an integer from 1 to 16. Correspondingly, the host cells express fusion proteins containing N copies of Magainin derivative linked in tandem, in which N is preferably, N is an integer from 2 to 8. More preferably, N is either 4 or 8. The fusion protein does not contain any other carrier proteins.

The genetically engineered bacterial strains of the present invention are cultured under appropriate conditions to produce and accumulate fusion proteins composed of N copies of the linked polypeptides. The culturing conditions such as culturing media, temperature, humidity and pH value are apparent to one skilled in the art.

After the host cells have grown to a proper density, they can be harvested, e.g., by centrifugation. The harvested cells are then ruptured by physical or chemical methods, and the resulting product is collected and subject to further purification.

The microorganism cells expressing recombinant proteins can be ruptured by any conventional means, which may include, but are not limited to, freeze and thaw cycles, ultrasonic or mechanical treatment, or cellular lysis reagents. The selection of appropriate protocols to break up host cells is apparent to one skilled in the art.

The fusion proteins presented in the present invention are composed of multiple Magainin derivative peptides. Under suitable cleavage conditions and with proper substances, the fusion protein may be cleaved at the N-terminus of each Magainin derivative peptide, thereby producing multiple Magainin derivative peptides.

Since the C-terminus of Magainin derivative is an Arg residue, in another preferred embodiment of the present invention, the protease trypsin was used to specifically cleave the peptide bond formed by the participation of the carboxyl group of Arg. In this situation, it may be necessary to alter trypsin reaction conditions to prevent trypsin cleavage at internal Lys residues.

Alternatively, various anhydrides may be used in this process to protect any internal Lys residue or residues from cleavage by trypsin. For example, the present invention specifically contemplates acetylation of the two internal Lys residues of Magainin derivative by acetic anhydride, citraconic anhydride, or 3,4,5,6-tretrahydophthaloyl anhydride as a superior alternative for the protection of these residues from trypsin cleavage. As a result, trypsin can be used to specifically cleave the peptide bond formed by the participation of the carboxyl group of Arg without cleaving at any Lys residues. Therefore one step of cleavage can yield multiple Magainin derivative peptides.

In accordance with a preferred embodiment with the method of the present invention, acetylation of the internal $Lys_4$, $Lys_{10}$, $Lys_{11}$ and $Lys_{14}$ residue in Magainin may be accomplished by acetylation of the $\epsilon$-$NH_2$ in the Lys residues. Such acetylation is conducted by, e.g., suspending the purified wet inclusion body in a $Na_2CO_3$ solution, and then gradually adding maleic anhydride derivatives to the solution with stirring at room temperature at pH 8. After 4 hours, the reaction mixture is dialysed overnight in phosphate buffer, and the fusion protein in the dialyzed reaction mixture is digested with trypsin at a ratio of protein-to-trypsin of about 1000:0.5–2 (w/w) at 30° C. for 2 hours. During the reaction, digestion is monitored by HPLC analysis.

After digestion, the acyl group from the $\epsilon$-$NH_2$ is deprotected by acidifying the reaction mixture to pH 2.0–3.0 for 4–6 hours at room temperature using hydrochloric acid. Finally, the acidified reaction is neutralized with $NaHCO_3$ to pH 5.0, the precipitate is centrifuged, and the crude Magainin derivative is collected from the precipitate.

After fusion protein cleavage, highly purified polypeptide can be obtained via a series of separation and purification steps, e.g., by chromatographic methods. Such chromatographic methods may include, but are not limited to, ion-exchange, hydrophobic, size exclusion, and reverse phase chromatography. The media used in these methods may be purchased from commercial vendors, such as Amersham Pharmacia Biotech, Whatman, Merk KgaA, and Grace Vydac etc. Single chromatography or a combination of multiple chromatography steps may also be used in the purification processes. In general, HPLC is used as a means of purification. Typically, C18 reversed phase chromatography with a TFA-$CH_3CN$ system as mobile phase is utilized. These chromatographic methods are well known to one skilled in the art.

It should be pointed out that, although the method to produce Magainin derivative peptide has been described hereinafter to illustrate the present invention, it should be apparent to one skilled in the art based on the disclosure presented herein that such method can also be used to produce Magainin analogs, as long as the amino acid residue at the N-terminus and at the C-terminus of a Magainin derivative analog can form a specifically cleavable peptide bond with the neighboring amino acid residue(s), while the cleavage will not occur internally within the polypeptide. Therefore, methods to produce Magainin analogs by ligating genes in tandem are within the scope of the present invention.

With regard to the production of Magainin derivative, the recombinant methods of the present invention have a number of advantages over other methods. Chemical synthesis of Magainin derivative, for example, is technically demanding, and the cost of such synthesis is high.

Pharmaceutical Compositions

The Magainin derivatives of the present invention can be incorporated into pharmaceutical compositions. Such compositions typically include the Magainin derivatives of the present invention (synonymously, "active compound") and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; anitioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline; bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars polyalcohols such as mannitol, sorbitol, sodium chloride in the composition. Prolonged absorption of the injectable compositions can be brought about by including in the composition an agent which delays absorption for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as micro crystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with maonoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral, buccal, parenteral or inhalation compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic erect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and thereby reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein or polypeptide can include a single treatment or, preferably, can include a series of treatments.

The present invention is further illustrated by the following examples, which should not be construed as limiting, but are merely exemplary in nature. The contents of all references, patents and published patent applications cited throughout this application are incorporated herein by reference.

EXAMPLES

Example 1

Preparation of the Magainin($Leu_{21}$, $Ser_{23}$, $Arg_{24}$) by Bioengineering Techniques 1. Construction of a Plasmid Containing One Copy of the Gene Encoding Magainin ($Leu_{21}$, $Ser_{23}$, $Arg_{24}$)

A. Synthesis of Gene Fragments

The following gene fragments were synthesized by the amino acid sequence of ($Leu_{21}$, $Ser_{23}$, $Arg_{24}$) in Shanghai Genecore Biotechnologies Co., Ltd.

```
                                                                    [SEQ ID NO.:19]
F₁: 5' AAT TCC AGA TCT CGT ATG GGT ATC GGT AAA TTT CTG CAC AGC GCG AAA AAA 3'

[SEQ ID NO.:20]
F₂: 5' TTT GGT AAA GCG TTT GTG GGT GAA ATC CTG AAC AGC CGT TAG GGA TCC A 3'

[SEQ ID NO.:21]
F₃: 5' AG CTT GGA TCC CTA ACG GCT GTT CAG GAT TTC ACC CAC AAA CGC TTT 3'

[SEQ ID NO.:22]
F₄: 5' ACC AAA TTT TTT CGC GCT GTG CAG AAA TTT ACC GAT ACC CAT ACG AGA TCT GG 3'
```

B. Litigation of DNA Fragments

The systemized fragment $F_1$, $F_2$, $F_3$ and $F_4$ with optical density at 260 nm ($A_{260nm}$) equaling to 2 were dissolved in 40 µl sterile water, respectively, 2.5 µl of fragment $F_1$ and $F_4$ were drawn into one tubes separately, while 2.5 µl of fragment $F_2$ and $F_3$ were put into in another tube separately. To the two tubes, 1 µl of $T_4$ polylnucleotide kinase, 1 µl of 10×$T_4$ polylnucleotide kinase buffer, 0.5 µl of ATP with a concentration of 0.1 mol/L, and 2.5 µl of sterile water were added respectively.

The reaction mixture was incubated at 37° centigrade for 60 minutes, then incubated in a water bath at 95° centigrade for 10 minutes to make T4 kinase inactives, and then was naturally cooled down to room temperature to complete the anneal of complementary DNA fragments.

1 µl of $T_4$ Ligase and 2 µl of the $T_4$ Ligase buffer were added. The mixture was incubated overnight at 15° centigrade for litigation.

The contemplated DNA fragments after litigation could encode Magainin ($Leu_{21}$, $Ser_{23}$, $Arg_{24}$) having amino acid sequence shown as below:

The plasmid pUC8 was double digested with EcoRI and Hind III, 10 µl (about 1 µg) of pUC8, 0.5 µl of EcoRI, 0.5 µl of Hind III, 2.0 µl of muticore buffer, 0.2 µl of FBSA, and 6.8 µl sterile water were added into a tube, and the reaction mixture was incubate at 37° centigrade for 2 hours. The digested vector was purified and recovered by electrophoresis through low melting point agrose, then precipitated by alcohol, and dissolved in 10 µl of sterile water.

0.5 µl of the digested plasmid pUC8 was ligated with the DNA fragment obtained from step B, the ligation reaction was conducted at 16° centigrade for 5 hours.

The bacterial cells of *E.coli* JM103 JM103, JM 109 or DH5α was cultured and treated with calcium chloride for preparing the competent bacterial cells, according to the procedures described in Molecular Cloning: a Laboratory Manual, published by Cold Spring Harbor Laboratory Press. The product resulted from ligation of the digested plasmid and the DNA fragment was added into 100 µl competent bacterial cells for transformation. The transformed bacterial cells were incubated on ice for 30 minuets, then incubated at 42° centigrade for 2 minuets, and again incubated on ice for 2 minuets. The bacterial cells were added into 300 µl of LB liquid media, followed by incubation at 37° centigrade for 1 hour. Bacterial cells were spread on a plate containing LB media and ampicillin antibiotic, and incubated overnight at 37° centigrade. Single colonies were screened in the following day, from which the recombinant plasmid was extracted. The DNA sequencing of the recombinant plasmid was performed on a sequence analyzer. The recombinant plasmid contains two copies of the gene encoding Magainin ($Leu_{21}$, $Ser_{23}$, Arg24) is referred as pUC-M1.

```
EcoR I                                           Bbgl II
Asn Ser Arg Ser Arg Met Gly Ile Gly Lys Phe Leu His Ser Ala Lys Lys Phe Gly Lys

AAT TCC AGA TCT CGT ATG GGT ATC GGT AAA TTT CTG CAC AGC GCG AAA AAA TTT GGT AAA

GG TCT AGA GCA TAC CCA TAG CCA TTT AAA GAC GTG TCG CGC TTT TTT AAA CCA TTT

[SEQ ID NO.23]
Ala Phe Val Gly Glu Ile Leu Asn Ser Arg Stop Gly Ser

[SEQ ID NO.24]
GCG TTT GTG GGT GAA ATC CTG AAC AGC CGT TAG GGA TCC A

[SEQ ID NO.25]
CGC AAA CAC CCA CTT TAG GAC TTG TCG GCA ATC CCT AGG TTC GA
                                                   Bam HI  Hind III
```

II. Construction of a Plasmid Containing Multiple Copies of the Gene Encoding Magainin (Leu$_{21}$, Ser$_{23}$, Arg$_{24}$)

A. Synthesis of Gene Fragments

The following gene fragments were synthesized by the amino acid sequence of (Leu$_{21}$, Ser$_{23}$, Arg$_{24}$) in Shanghai Genecore Biotechnologies Co., Ltd.

```
F₁': 5'-AAT TCC AGA TCT CGT GGT ATC GGT AAA TTT CTG CAC AGC GCG AAA AAA-3'

F₂': 5'-TTT GGT AAA GCG TTT GTG GGT GAA ATC CTG AAC AGC CGT GGA TCC TAG A-3'

F₃': 5'-AG CTT CTA GGA TCC ACG GCT GTT CAG GAT TTC ACC CAC AAA CGC TTT-3'

F₄': 5'-ACC AAA TTT TTT CGC GCT GTG CAG AAA TTT ACC GAT ACC ACG AGA TCT GG-3'
```

B. Litigation of DNA Fragments

The systemized fragment F$_1$', F$_2$', F$_3$' F$_4$' with optical density at 260 nm (A$_{260nm}$) equaling to 2 were dissolved in 40 μl sterile water, respectively, 2.5 μl of fragment F$_1$' and F$_4$' were drawn into one tubes separately, while 2.5 μl of fragment F$_2$' and F$_3$' were put into in another tube separately. To the two tubes, 1 μl of T$_4$ polynucleotide kinase, 1 μl of 10×T$_4$ polynucleotide kinase buffer, 0.5 μl of ATP with a concentration of 0.1 mol/L, and 2.5 μl of sterile water were added respectively.

The reaction mixture was incubated at 37° centigrade for 60 minutes, then incubated in a water bath at 95° centigrade for 10 minutes to make T4 kinase inactives, and then was naturally cooled down to room temperature to complete the anneal of complementary DNA fragments.

1 μl of T$_4$ Ligase and 2 μl of the T$_4$ Ligase buffer were added. The mixture was incubated overnight at 15° centigrade for litigation.

The contemplated DNA fragments after litigation could encode Magainin (Leu$_{21}$, Ser$_{23}$, Arg$_{24}$) having amino acid sequence shown as below:

```
EcoR I BgL II
Asn Ser Arg Ser Arg Gly Ile Gly Lys Phe Leu His Ser Ala Lys Lys Phe Gly Lys
AAT TCC AGA TCT CGT GGT ATC GGT AAA TTT CTG CAC AGC GCG AAA AAA TTT GGT AAA
    GG TCT AGA GCA CCA TAG CCA TTT AAA GAC GTG TCG CGC TTT TTT AAA CCA TTT

Ala Phe Val Gly Glu Ile Leu Asn Ser Arg Gly Ser stop
GCG TTT GTG GGT GAA ATC CTG AAC AGC CGT GGA TCC TAG A
CGC AAA CAC CCA CTT TAG GAC TTG TCG GCA CCT AGG ATC TTCGA
                                                BaM H I Hind III
```

The plasmid pUC8 was double digested with EcoRI and Hind III. 10 μl (about 1 μg) of pUC8, 0.5 μl of EcoRI, 0.5 μl of Hind III, 2.0 μl of muticore buffer, 0.2 μl of BSA, and 6.8 μl sterile water were added into a tube, and the reaction mixture was incubate at 37° centigrade for 2 hours. The digested vector was purified and recovered by electrophoresis through low melting point agrose, then precipitated by alcohol, and dissolved in 10 μl of sterile water.

0.5 μl of the digested plasmid pUC8 was ligated with the DNA fragment obtained from step B, the ligation reaction was conducted at 16° centigrade for 5 hours.

C. Transformation

The bacterial cells of E.coli JM103, JM103, JM 109 or DH5α was cultured and treated with calcium chloride for preparing the competent bacterial cells, according to the procedures described in Molecular Cloning: a Laboratory Manual, published by Cold Spring Harbor Laboratory Press. The product resulted from ligation of the digested plasmid and the DNA fragment was added into 100 μl competent bacterial cells for transformation. The transformed bacterial cells were incubated on ice for 30 minuets, then incubated at 42° centigrade for 2 minuets, and again incubated on ice for 2 minuets. The bacterial cells were added into 300 μl of LB liquid media, followed by incubation at 37° centigrade for 1 hour. Bacterial cells were spread on a plate containing LB media and ampicillin antibiotic, and incubated overnight at 37° centigrade. Single colonies were screened in the following day, from which the recombinant plasmid was extracted. The DNA sequencing of the recombinant plasmid was performed on a sequence analyzer. The recombinant plasmid contains two copies of the gene encoding Magainin (Leu$_{21}$, Ser$_{23}$, Arg$_{24}$) is referred as pUC-M1.

D. Construction of a Plasmid Containing Two Copies of the Gene Encoding Magainin (Leu$_{21}$, Ser$_{23}$, Arg$_{24}$)

As shown in FIG. 1, part of the pUC-M1 plasmids were digested with BamHI and Hind III at 37° centigrade for 2 hours. The reaction mixture was composed of 10 μl (about 3 μg) pUC-M1, 0.5 μl of BamHI, 0.5 μl of Hind III, 2 μl of Buffer E, 0.2 μl of BSA, and 6.8 μl of H$_2$O. The digested plasmids (referred as pUC-M1 Ba/H) were recovered through electrophoresis on a low melting point agrose, precipitated with alcohol, and dissolved in 10 μl of water.

Another part the pUC-M1 plasmids were digested with Bgl II and Hind III at 37° centigrade for 2 hours. The reaction mixture was composed of 10 μl (about 3 μg)pUC-M1, 0.5 μl of Bgl II, 0.5 μl of Hind III, 2 μl of Buffer B, 0.2 μl of BSA, and 6.8 μl of H$_2$O. The digested small fragment (referred as M1Bg/H) was recovered through electrophoresis on a low melting point agrose, precipitated with alcohol, and dissolved in 10 μl of water.

Then, pUC-M1 Ba/H and M1Bg/H were ligated under the existence of DNA ligase. The reaction mixture comprising 1 μl of pUC-M1 Ba/H, 1 μl of M1Bg/H, 1 μl T$_4$ Ligase, 1 μl of 10×T$_4$ Ligase buffer and 6 μl of water were incubated at 16° centigrade for 5 hours.

The resulted product after the above ligation reaction was transformed into the competent bacterial cells, followed by cultivating the transformed bacterial cell overnight at 37° centigrade, Single colonies were screened and the recombinant plasmids were extracted according to the procedures described above.

The desired recombinant plasmid (referred as pUC-M2) contains two copies of the gene encoding Magainin (Leu$_{21}$, Ser$_{23}$, Arg$_{24}$) with the length about 200 bp.

F. Construction of a Plasmid Containing Four, Eight and Sixteen Copies of the Gene Encoding Magainin (Leu$_{21}$, Ser$_{23}$, Arg$_2$)

Still, as shown in FIG. 1, part of the pUC-M2 plasmids were digested with Bam II and Hind III at 37° centigrade for 2 hours, the digested plasmids (referred as pUC-M2 Ba/H) were recovered through electrophoresis on a low melting point agrose. While another part of the pUC-M1 plasmids were digested with Bsgl II and Hind III at 37° centigrade for 2 hours, the digested small fragment containing two copies of the gene encoding Magainin (Leu$_{21}$, Ser$_{23}$, Arg$_{24}$) (referred as M2 Bg/H) was recovered through electrophoresis on a low melting point agrose. The recovered fragments of pUC-M2 Ba/H and M2 Bg/H were precipitated with alcohol, and dissolved in 10 μl water respectively.

pUC-M2 Ba/H and M2Bg/H fragments were ligated under the existence of T$_4$ DNA ligase. Ligation of the fragments, transformation into bacterial cells, and screening of the recombinant plasmid were conducted as the procedures described in step E.

The desired recombinant plasmids (referred as pUC-M4) contains four copies of the gene encoding Magainin (Leu$_{21}$, Ser$_{23}$, Arg$_{24}$) were obtained.

By the similar method, the desired recombinant plasmids pUC-M8 and pUC-M16 were obtained, which respectively contain eight and sixteen copies of the gene encoding Magainin (Leu$_{21}$, Ser$_{23}$, Arg$_{24}$)

III. Fermentation and Expression

The bacterial strain harboring the plasmid containing one or multiple copies of the Magainin (Leu$_{21}$, Ser$_{23}$, Arg$_{24}$)-encoded gene was incubated in a shaking bottle with the capability of 1 liter (10 bottles in total), each containing 300 ml of LB liquid media consisted of 10 g of peptone, 5 g of yeast extract, 10 g/L of sodium chloride. 0.2 mM of Isopropyl beta-D-Thiogalactopyranoside (IPTG) was added at 37° centigrade for the induction of the protein to be expressed. The bacterial cells were incubated overnight and harvested by centrifugation. When using the plasmid with the temperature-controlled promotor P$_L$, the bacterial cells were cultured at 30° centigrade for eight hours. Then the temperature of the media was increased to 42° centigrade, and the bacterial cells were maintained for four hours to make the gene expressed.

The bacterial cell walls were broken up under the effect of lysozyme at 37° centigrade for an hour. The precipitate was treated with 6M of guanidine hydrochloride. After centrifugation, dialysis and further centrifugation steps, the inclusion bodies of protein were obtained. The inclusion bodies were washed three times, with the wash solution containing 1% sodium chloride, 0.1% Briton X-100 (obtained from Sigma Aldrich) and Tris-HCL buffer (20 mM, pH8). The fusion protein was identified through polyacrylamide gel electrophoresis (PAGE) containing 12% sodium dodecanesulphonate (SDS).

The inclusion bodies were dissolved in 8M of carbanide solution. Under the existence of 50 mM of hydrochloric acid, cyanogen bromide was added for the lysis of inclusion bodies. The solution was stirred with the protection of nitrogen and shunning of the light. After completion of the lysis reaction, crude product of the Magainin derivative was obtained through Sephadex G-25 with fast protein liquid chromatography (FPLC, AKTA™ manufactured by Amersham Pharmacia Biotech), and final product of the Magainin derivative was acquired through purification with high performance liquid chromatography (HPLC, C$_{18}$ column) and gradient elution with CH$_3$CN/0.1% TFA buffer. The HPLC analysis result of the obtained product is consistent with those products prepared by chemical synthesis.

In the fusion protein, an amino acid spacer of Asn-Ser-Arg-Ser-Arg is existed between the C-terminus of one Magainin (Leu$_{21}$, Lys$_{23}$, Arg$_{24}$) peptide and the N-terminus of the next Magainin (Leu$_{21}$, Lys$_{23}$, Arg$_{24}$) peptide. After acetylation of the internal Lys$_4$, Lys$_{10}$, Lys$_{11}$ and Lys$_{14}$ amino acid within the Magainin (Leu$_{21}$, Lys$_{23}$, Arg$_{24}$) peptide, separate peptides were resulted under the effect of trypsin.

Example 2

Preparation of the Magainin (Leu$_{21}$, Lys$_{23}$, Arg$_{24}$) by Solid Phase Synthesis A. Amino Acid Monomers Amino acid monomers used in the experiment were shown in table 1.

TABLE 1

| | |
|---|---|
| Fmoc-L-Ala-OH | Fmoc-L-Lys(Boc)-OH |
| Fmoc-L-Asn(Trt)-OH | Fmoc-L-Met-OH |
| Fmoc-L-Asp(OtBu)-OH | Fmoc-L-Phe-OH |
| Fmoc-L-Gln(Trt)-OH | Fmoc-L-Pro-OH |
| Fmoc-L-Glu(OtBu)-OH | Fmoc-L-Ser(tBu)-OH |
| Fmoc-L-Gly-OH | Fmoc-L-Thr(tBu)-OH |
| Fmoc-L-His(Trt)-OH | Fmoc-L-Trp-OH |
| Fmoc-L-Ile-OH | Fmoc-L-Tyr(tBu)-OH |
| Fmoc-L-Leu-OH | Fmoc-L-Val-OH |

In which:

Fmoc stands for 9-fluorenyl methoxycarbonyl, BOC for tert-butyloxycarbonyl, Trt for trityl, OtBu for tertiary butyl ester, and TBu for tert-butyl.

B. Apparatus and Reagents

Apparatus: Model 433A peptide synthesizer (Applied Biosystem, US)

Reagents:

N-methyl ketopyrrolidine, methylene chloride, hexahydropyridine, methanol, dimethylaminopyridine/DMF N, N-diisopropylethylamine/NMP, 100 mmole HBTU/0.5 M HOBT in DMF, N, N-Dicyclohexylcarbodiimide/NMP In which:

DMF stands for N, N-Dimethylformamide, NMP for N-methylpyrrolidone, HOBT for 1-Hydroxybenzotriazole, and HBTU for 2-(1H-benzotriazole-yl-1,1,3,3-tetramethyl-Uronium hexafluorophosphate).

C. Method a. Synthesis

Take the synthesis scale of 0.25 mmol for example, the synthesis process was described as follows, 0.25 g of HMP resin was weighed and placed in a reactor vessel of the synthesizer. 1 mmol of various residues, each coupled with protecting groups, were weighed and arrayed in the synthesizer by the amino acid sequence of the insulinotropic peptide derivate from the carboxy terminal to the amino terminal. At room temperature of 25° centigrade, reactions for removing Fmoc protection, activating a residue and attaching the activated residue to HMP resin were automatically performed under the control of a computer program, Such reactions were circulated until the whole peptide was synthesized. After completion of the synthesis, the residue-attached resin, with each residue coupled with side chain protecting groups, was air dried on a peptide synthesizer and then weighed.

b. Removal of Protecting Groups and Detachment of Resin

The residue-attached resin, with each residue of the insulinotropic peptide derivative coupled with protecting groups, was placed in a plugged erlenmeyer flask, and followed by addition of cleavage reagents as shown in table 2.

TABLE 2

| Reagent | Dosage |
| --- | --- |
| Water | 0.50 ml |
| Methyl phenate | 0.50 ml |
| Phenol | 0.75 g |
| Mercaptoethanol | 0.20 ml |
| trifluoroacetic acid | 10.0 ml |

The electromagnetic stirring reaction was carried out at constant temperature of 30° centigrade for 6 hours. After filtration step, the aqueous filtrate was collected. The resin was washed with small amount of trifluoroacetic acid. Then the collected aqueous filtrate and the washing solution were mixed together, and ether was added for precipitation. The mixture was filtrated, and the resulted precipitate was washed with small amount of ether. After evaporation in a dehumidifier, the crude product was obtained.

c. Purification by HPLC and Lyophilization

Separation and purification of the crude product was achieved by using preparative HPLC. Final product was obtained after the steps of freezing and lyophilization. Through joint analysis of chromatogram and mass spectrogram, the molecular weight of the derivative was found to be consistent with the theoretical value.

Example 3

Anti-microbial Effects Studies

The anti-microbial effect of the Magainin($Leu_{21}$, $Ser_{23}$, $Arg_{24}$) was conducted according to the following procedures, with the comparison of that of the naturally occurring Magainin.

The bacterial strain of *Escherichia coli* JM103 and *staphylococcus aureus* were employed.

The bacteria were cultivated at 37° centigrade, and diluted to $1 \times 10^6$ bacteria/ml. 20 mM of the sterilized Tris-HCl buffer (pH6.5) was added. Then the Magainin derivative and the naturally occurring Magainin II with various concentrations were added respectively, and incubated at 37° centigrade for different time, 50 μl of the cultures was taken and spread on an agar plate, and incubated at 37° centigrade overnight. The remaining bacteria colonies were accounted for, and the percent of the killed bacteria was calculated.

The ant-microbial effects of Magainin ($Leu_{21}$, $Ser_{23}$, $Arg_{24}$) were tested with comparison with that of the naturally occurring Magainin II. As shown in table 3, Magainin ($Leu_{21}$, $Ser_{23}$, $Arg_{24}$) had shown obvious ant-microbial effects on *Escherichia coli*, which is similar to that of the naturally occurring Magainin. The anti-microbial effect of Magainin ($Leu_{21}$, $Ser_{23}$, $Arg_{24}$) on *Staphylococcus aureus* can be seen from table 4, and the result of time-kill study of Magainin ($Leu_{21}$, $Ser_{23}$, $Arg_{24}$) was shown in FIG. 1.

TABLE 3

| Sample | Concentration μg/ml | Bacteria colonies remained 0 hr | Bacteria colonies remained 3 hr | Bacteria colonies remained 4 hr | Bacteria killed % 3 hr | Bacteria killed % 4 hr |
| --- | --- | --- | --- | --- | --- | --- |
| Magainin ($Leu_{21}$, $Ser_{23}$, $Arg_{24}$) | 0 | 407 228 317 | | | | |
| | 10 | | 109 73 91 | 160 195 177 | 71.3 | 44.2 |
| | 20 | | 9 5 7 | 2 5 3 | 97.8 | 99.1 |
| Naturally occurring Magainin | 10 | | 99 57 78 | 52 44 48 | 75.4 | 84.9 |
| | 20 | | 12 4 8 | 6 4 5 | 97.5 | 99.2 |

TABLE 4

| Concentration μg/ml | Bacteria colonies remained 0 hour | Bacteria colonies remained 1 hour | Bacteria colonies remained 2 hours | Bacteria killed within 2 hours % |
| --- | --- | --- | --- | --- |
| 0 | 267 225 | | | |
| 50 | 158 185 172 | 18 18 18 | 2 2 2 | 99 99 99 |

Example 4

Hemolysis Test 3 ml of 0.9% sodium chloride solution was added into three tubes separately, followed by addition of 100 μl blood derived from SD rat (provided by Shanghai Laboratory Animal Center, Chinese Academic Sciences) respectively.

As a negative control, the naturally occurring Magainin peptide (obtained from Sigma) was dissolved in sterile water, and the Magainin peptide solution with a concentration of 1 mg/ml was prepared. 300 μl, 1.5 ml and 3 ml of such solution were added into three tubes respectively. After incubation at room temperature for 30 minutes, centrifugation was conducted at 3000 rpm, and supernates in three tubes was taken to determine the optical density at 590 nm with a spectrophotometer.

In the testing group, Hemolysis effect of the Magainin (Leu$_{21}$, Ser$_{23}$, Arg$_{24}$) was examined. Magainin (Leu$_{21}$, Ser$_{23}$, Arg$_{24}$) peptide was dissolved in sterile water to prepare the solution with a concentration of 1 mg/ml, 300 µl, 1.5 ml and 3 m of the solution were added into three tubes respectively, and the hemolysis test was conducted using the same method as applied to the negative control group.

In the positive control group, 0.1% of Triton X-100 (obtained from Sigma Aldrich) was employed aid the hemolysis test was performed according to the steps prescribed above.

In this test, erythrocyte will be precipitated after centrifigation and supernate appear red in the circumstance hemolysis has occurred. As shown in table 5, hemolysis to erythrocytes was not observed in the testing group, even using Magainin (Leu$_{21}$, Ser$_{23}$, Arg$_{24}$) at a concentration of 1000 µg/ml.

TABLE 5

| Group | | Dosage (µg/ml) | Hemolysis % |
|---|---|---|---|
| Negative Control Group | Naturally-occurring Magainin | 100 | 0 |
| | | 500 | 0 |
| | | 1000 | 1.9 |
| Testing Group | Magainin (Leu$_{21}$, Ser$_{23}$, Arg$_{24}$) | 100 | 0 |
| | | 500 | 0 |
| | | 1000 | 2 |
| Positive Control Group | Tritonx-100 | 0.1% | 100 |

Example 5

Acute Toxicity Test

Six mice of Kun-ming species were divided into three groups randomly. Mice in the first group were intraperitoneally injected with 100 µg Magainin (Leu$_{21}$, Ser$_{23}$, Arg$_{24}$) which is prepared by the method described in example 1, Mice in the second group were injected with 200 µg Magainin (Leu$_{21}$, Ser$_{23}$, Arg$_{24}$), while those in the third group were injected with 1000 µg Magainin (Leu$_{21}$, Ser$_{23}$, Arg$_{24}$). The toxicity of Magainin (Leu$_{21}$, Ser$_{23}$, Arg$_{24}$) was determined by observing the influence of injection to the survival of the mice. As shown in table 6, during the observation period of one week, which is long enough to show the influence of injection under the current dosage, mice in the three groups all survived from injection, which indicates the safety of using Magainin (Leu$_{21}$, Ser$_{23}$, Arg$_{24}$) in animal.

TABLE 6

| Dosage of Intraperitoneal Injection | Livability |
|---|---|
| 100 µg | 100% |
| 200 µg | 100% |
| 1000 µg | 100% |

Although the preferred embodiments and figures of this invention have been described in previous paragraphs, it should be apparent to one skilled in the art that modifications and alternative editions of this invention are possible, and substantially identical methods and substances are still within the scope of this invention, which is set forth in the following claims.

What is claimed is:

1. A Magainin derivative peptide having the amino acid sequence of the general formula:

Gly-Ile-Gly-Lys-Phe-Leu-His-Ser-Ala-Lys-Lys-Phe-Gly-Lys-Ala-Phe-Val-Gly-Glu-Ile-Xaa-Asn-Xaa-Arg-OH [SEQ ID NO.: 16] in which:

Xaa at position 21 is an amino acid selected from the group consisting of Met, Ile and Leu;

Xaa at position 23 is an amino acid selected from the group consisting of Ser, Lys, Ile, Leu and Arg, and wherein Xaa at position 21 is not Met when Xaa at position 23 is Ser.

2. The peptide of claim 1, wherein said peptide has an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15.

3. The peptide of claim 2, wherein said peptide has an amino acid sequence selected from the group consisting of SEQ ID NO: 2, SEQ ID NO: 4, SEQ ID NO: 5, SEQ ID NO: 6, SEQ ID NO: 7, SEQ ID NO: 8, SEQ ID NO: 10, SEQ ID NO: 11, SEQ ID NO: 12, SEQ ID NO: 13 and SEQ ID NO: 15.

4. The peptide of claim 3, wherein said peptide has an amino acid sequence selected from the group consisting of SEQ ID NO: 6 and SEQ ID NO: 11.

5. The peptide of claim 4, wherein said peptide has an amino acid sequence as shown in SEQ ID NO: 11.

6. A fusion peptide comprising at least two tandemly linked peptides wherein each amino acid sequence has the general formula shown below:

Gly-Ile-Gly-Lys-Phe-Leu-His-Ser-Ala-Lys-Lys-Phe-Gly-Lys-Ala-Phe-Val-Gly-Glu-Ile-Xaa at position 21-Asn-Xaa at position 23-Arg (SEQ ID NO: 16)

in which:

Xaa at position 21 is an amino acid selected from the group consisting of Met, Ile and Leu; and Xaa at position 23 is an amino acid selected from the group consisting of Ser, Lys, Ile, Leu and Arg.

7. A pharmaceutical composition comprising a Magainin derivative peptide of claim 1 and a pharmaceutically acceptable carrier and/or pharmaceutically compatible binding agents.

8. A pharmaceutical composition, comprising a Magainin derivative peptide of claim 3 and a pharmaceutically acceptable carrier and/or pharmaceutically compatible binding agents.

9. A pharmaceutical composition, comprising a Magainin derivative peptide of claim 4 and a pharmaceutically acceptable carrier and/or pharmaceutically compatible binding agents.

10. A pharmaceutical composition, comprising a Magainin derivative peptide of claim 5 and a pharmaceutically acceptable carrier and/or pharmaceutically compatible binding agents.

* * * * *